(12) United States Patent
Fields et al.

(10) Patent No.: US 7,959,658 B2
(45) Date of Patent: Jun. 14, 2011

(54) HEATING SYSTEM TO ALLEVIATE HYPOTHERMIA

(75) Inventors: R. Wayne Fields, Brookings, OR (US); Melvin F. Campf, Tigard, OR (US); Larry I. Crawshaw, Portland, OR (US); Habib Homayoun, Beaverton, OR (US); Gary Mills, Gladstone, OR (US); John D. Robinson, Spokane, WA (US); Gerald Recktenwald, Portland, OR (US); Pete Chambers, Vienna, VA (US)

(73) Assignee: ThermoGear, Inc., Lake Oswego, OR (US)

( * ) Notice: Subject to any disclaimer, the term of this patent is extended or adjusted under 35 U.S.C. 154(b) by 1026 days.

(21) Appl. No.: 11/419,186

(22) Filed: May 18, 2006

(65) Prior Publication Data

US 2007/0049997 A1  Mar. 1, 2007

Related U.S. Application Data

(60) Provisional application No. 60/682,531, filed on May 18, 2005.

(51) Int. Cl.
*A61F 7/00* (2006.01)
(52) U.S. Cl. .......................... 607/104; 607/96
(58) Field of Classification Search .............. 607/96, 607/104
See application file for complete search history.

(56) References Cited

U.S. PATENT DOCUMENTS

| | | | |
|---|---|---|---|
| 3,443,066 A | 5/1969 | Weibel | |
| 3,989,924 A | 11/1976 | Kurtzer | |
| 4,353,359 A * | 10/1982 | Milbauer | 601/166 |
| 4,950,868 A | 8/1990 | Moss et al. | |
| 5,269,369 A * | 12/1993 | Faghri | 607/104 |
| 5,383,918 A | 1/1995 | Panetta | |
| 6,375,673 B1 * | 4/2002 | Clifton et al. | 607/104 |
| 2002/0019654 A1 * | 2/2002 | Ellis et al. | 607/98 |
| 2002/0156509 A1 * | 10/2002 | Cheung | 607/96 |
| 2003/0069621 A1 | 4/2003 | Kushnir | |
| 2003/0236561 A1 * | 12/2003 | Lennox | 607/104 |
| 2004/0225341 A1 * | 11/2004 | Schock et al. | 607/104 |
| 2006/0004426 A1 * | 1/2006 | Heaton | 607/104 |

FOREIGN PATENT DOCUMENTS

FR 2577390 A1 8/1986
WO 2004/006814 A2 1/2004
* cited by examiner

Primary Examiner — Roy D Gibson
Assistant Examiner — Kaitlyn E Helling
(74) Attorney, Agent, or Firm — Schwabe, Williamson & Wyatt

(57) ABSTRACT

A medical, electrically powered thermal cover for fitting predominantly the trunk and head of a person experiencing or potentially experiencing traumatic or cold-exposure hypothermia. The thermal cover encases all of the torso and neck, and portions of other body areas. Heating may be distinctly non-uniform, being applied to the body surface only in special regions where the body's capacity for heat uptake may be relatively high. In sum, the system may monitor deep body core temperature, direct heat to the body core where it may be most needed, and controls therapy over time to restore normothermia.

5 Claims, 3 Drawing Sheets

HEATING SYSTEM TO ALLEVIATE HYPOTHERMIA

RELATED APPLICATION

This application is a non-provisional application claiming priority from provisional application No. 60/682,531 filed on May 18, 2005.

FIELD OF INVENTION

This invention relates to heating systems for maintaining or restoring normothermia in persons who are potentially or actually hypothermic, particularly during preparation, staging and transport from a remote location to a relevant medical facility.

BACKGROUND OF THE INVENTION

It is known that significant trauma or cold exposure to a person often induces hypothermia (health threatening reduction of core body temperature), which can compound medical consequences. Thus, it is desirable to provide additional heat in addition to normal body-generated heat, e.g., apply warming covers to the injured person.

It is preferred that the covers are provided with electric or other active heating to enhance the warming properties of the covers. However, known warming covers as applied to an injured person have problems. For example, skin should not be heated to a temperature of 105° F. or more, to avoid burns. Also, prior warming covers indiscriminately warm the limbs along with other areas, but heating the limbs of a significantly hypothermic person can release cold pooled blood into the core circulation that can then lead to serious circulatory problems in some patients. Finally, the body's capacity to take up externally applied heat varies considerably from one body surface locale to another. These important factors argue for selective heating of different body regions while avoiding or relatively reducing e.g. limb warming, a major departure from the prior art of passive or even active warming of a victim of trauma-induced or direct (e.g., cold exposure) hypothermia.

BRIEF SUMMARY OF THE INVENTION

Applicants' physiological and thermodynamic research indicates that effective rewarming of a significantly hypothermic human: a) greatly exceeds the capacity of passive warming; b) preferably avoids or reduces major limb rewarming; and c) the active application of heat is preferably selectively applied to accommodate large locale-dependent variations in body surface heat uptake capabilities. The areas most conducive to efficient heat uptake are the head, neck, chest (including the shoulders and armpits; hereafter, "chest" shall denote the extended area) and abdomen. It has also been determined for one embodiment that the heat-generating covering may be preferably tight fitting or otherwise in good contact for more efficient transfer of heat to the body surface and ultimately the body core (in general, deep structures of the torso, neck and head). Restoring body core temperature to normal is typically the goal of therapy.

To accomplish some of these objectives, exemplary embodiments of the thermal covers are provided herein.

In one embodiment, a heating system is disclosed that may be considered to be relatively aggressive in treatment of hypothermia. This may be similar to a close-fitting jump suit, which substantially envelopes of the entire body, except for, in certain embodiments, the face and the distal two-thirds of the limbs. Such a design can be viewed as a modified jump suit in two basic parts, configured much like a hooded sleeping bag that can be completely unzipped to separate a bottom half that lies on a supporting surface, and a top half that may be separate and removable. For example, one could envision the bottom half of the thermal cover laid flat, the subject placed longitudinally on said bottom half, and then the top half placed over the subject and fastened around the entire mutual circumferences of the top and bottom halves. A close fit may be aided by the modest tension which arises from special cover design features as described later.

For the aggressive treatment example, several structural and functional modifications of today's typical jump suit are desired to present structure and function. First, the arm and leg elements may be shortened so that only short lengths extend from the torso. This facilitates patient insertion and better guards against significant stray heating of the limbs. Second, as described, the jump suit may be entered and closed around the sides of a supine subject, not, for example, circumferentially at the waist, to aid patient insertion and to optimize any need to occasionally access trauma sites anywhere along the long axis of the subject. Third, the head and neck may be covered by connecting flaps that extend from either the top or bottom jump suit halves. Fourth, the jump suit exit openings for each arm and leg are loosely conforming, not tightly sealed, to permit minor heat leakage from within the actively heated jump suit (more details later). Fifth, with regard to the head hood, a purse-string or other means may be employed to create a reasonably good seal to prevent heat leakage around the face perimeter. Note that some leakage may be acceptable at the arm and leg exits (explained later), but may be undesirable at the opening for the face. Finally, the modified jump suit features active heating, to address the extraordinary quantity of heat desired to restore normothermia in a severely or moderately hypothermic subject. The heating element may be preferably a distributed pattern of thermal wire or a heat conducting fabric or gel that may be electrically heated by portable power means, e.g., batteries. However, other forms of active heating power (e.g., fuel-based or phase-change processes) and distribution (e.g., circulating fluid, ceramic elements, or carbon-based materials) are potentially available as well.

In another embodiment, the design may be an elongate one piece unit having a first portion that extends from under the head and along the back of a patient i.e. to the patient's feet, and then may be wrapped up and around the feet and over the front of the patient to the patient's neck. The edges of both portions are provided with matable fasteners to substantially enclose the patient's body. A head cover may be desirable as well.

In various embodiments, two or more related levels of heating may be applied using the heat-generating cover, one relatively high and the other much lower. Temperature may be set by a single user control, so the two temperature levels are always in a fixed ratio, say four to one. The high temperature component may be applied to four parallel locales termed Primary Zones of heating (head, neck, chest and abdomen). All Primary Zones are integral to the top half of the heat-generating cover. In turn, one large Secondary Zone, occupying most of the subject's back and buttocks, represents the only area where the low temperature intensity is applied.

To recognize the many major departures of the present invention relative to the typical jump suit prototype, the core encapsulation and heating device shall be termed a thermal cover. Note that in the described configuration, all Primary Zones for warming are preferably formed as part of the top half of the thermal cover. We also position Secondary Zones for warming, preferably set in a fixed relative intensity of one-fourth that of the Primary Zones, so that they all lie on the bottom half of the thermal shell.

A second consideration is to provide adjustment of the thermal cover to persons of different sizes. This may be accomplished by the provision of expanders, i.e., expansion strips that are strategically positioned in the thermal cover.

The invention will be more fully appreciated upon reference to the following detailed description having reference to the accompanying drawings.

DETAILED DESCRIPTION

Figure 1:
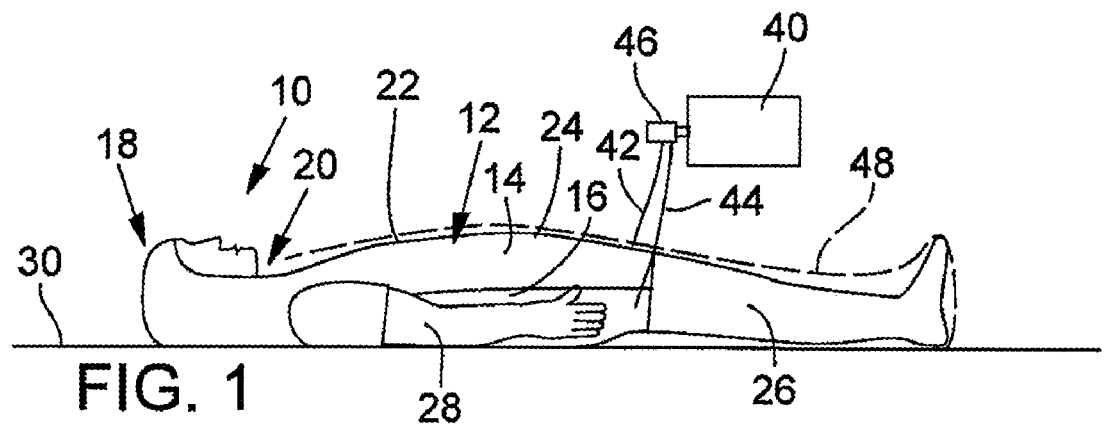
FIG. 1 illustrates an injured person having a medical thermal cover of the exemplar aggressive embodiment of the present invention.

FIG. 1 illustrates an injured person 10 enclosed in a medical thermal cover of an exemplar aggressive embodiment 12. The thermal cover 12 may be comprised of a top portion 14 (shown in top view in FIG. 3) and a bottom portion 16 (shown in top view in FIG. 2).

It is determined that major portions (Zones) of four areas of a person's body have optimum peripheral and deep blood flow for dispensing heat: (a) most or all of the head 18 (excluding the face); (b) most or all of the neck 20; (c) most or all of the chest 22 (including the shoulders and armpits as well); and (d) most or all of the abdomen 24. The latter four Zones may be in the upper body portion (subject supine as shown in FIG. 1) or the front side body portion (subject upright). Thus, the thermal cover may be split to provide top portion 14 and bottom portion 16 whereby the top portion 14 of the thermal cover contains sizeable sub-areas (Zones) that constitute the four Primary Zones for active heating, while the bottom portion 16 is in contact with the subject's lower body portion (the back and buttocks of the wearer), where one or more large sub-area of active low-level heating is referred to as Secondary Zone(s). Note that the Primary and Secondary Zones may not occupy the entire area of the respective thermal cover halves, since there are non-heated areas on both the top and bottom thermal cover halves that serve other purposes (described later). The exact number of zones may be subject to alternative groupings and that a given embodiment could use less or more total body area.

In one embodiment, the legs 26 and arms 28 may not be covered by the thermal cover 12 (except by short stubs extended from the body core) and this is desirable to preserve power, minimize cold blood from the limbs entering the core circulation, and also to provide ease of fitting the thermal cover to the patient. Such ease of fitting may be further enhanced by the two piece provision of the thermal cover. Thus, the bottom portion 16 may be laid out on a bed surface 30, e.g., of a transport litter or gurney. In one embodiment, the patient may be laid on the bottom portion, and wrap-around flap-based features integral to the bottom thermal cover half may be fitted to encompass the left and right upper thighs and the groin area. (See FIGS. 2 and 3.) Note that these features at the base of the legs are depicted as wrap-around flaps, but can be any of a number of arrangements to facilitate encasing of the patient's upper thigh and groin area in a manner that allows a reasonable fit and can be provided with active heating means. (The same rationale also applies to the shoulder-armpit, neck, and head encasing approaches to be described hereafter.) At this time, the head hood (76) and the neck wrap flaps (74) features integral to the top thermal cover half can be placed over the subject's head and then fitted by properly extending expander strips (neck flap expander strips not shown) and/or a purse-string or other means (not shown) to foster a seal around the perimeter of the opening for the face. The top half 14 of the thermal cover 12 may be placed on top of the supine patient, and to fasten it to the lower half 16 of the thermal cover around the entire available perimeter using the extensive string of fasteners on each top and bottom half (e.g., snap fasteners, Velcro strips, etc.).

In some embodiments, the thermal cover may be somewhat snug fitting to optimize the transfer of heat from the thermal cover to the body. Further, the fasteners, represented by "x"s or from the backside as circled "x"s, at points 34 are preferably independent fasteners (e.g., the fasteners can be unfastened independently of one another to selectively expose a body portion for treatment, i.e., a point of injury).

To accommodate different patient sizes, both the top and bottom halves of the thermal cover may be provided with longitudinal expanders 36 to accommodate girth differences and lateral expanders 38 to accommodate height differences. Expanders oriented at various angles to the longitudinal and lateral axes may also be included, to address different body configurations. The expanders 36 and 38 preferably are not heat producing. Depending on varying preferences, it may be desirable to provide expanders 36 near the side, head, or foot edges in the upper portion 12, either instead of or in addition to the expanders provided in the bottom portion. As noted, the lateral expanders that accommodate height differences are preferably provided for both top and bottom portions (14 and 16). The expanders can be of varying types, including elastic strips or accordion-type strips. The expanders are preferably inherently elastic, so that the only user action required is to extend the thermal cover in the desired direction, relevant expanders progressively extending within their range of action. All of the expanders exhibit a real but modest restoring force throughout the permissible range of travel provided by design. Thus, regardless of the ultimate configuration of thermal cover extension, the active expanders collectively impose a modest but real tension to aid a snug fit to the subject.

As previously mentioned, the thermal cover halves or portions may be provided with wrap-around strips to provide stub covering for the upper arms and thighs, and to further cover the groin and neck areas. It various embodiments, the desired covering of these areas can be provided in various ways and the coverings shown and described are but an example for accomplishing that objective.

Figure 2:
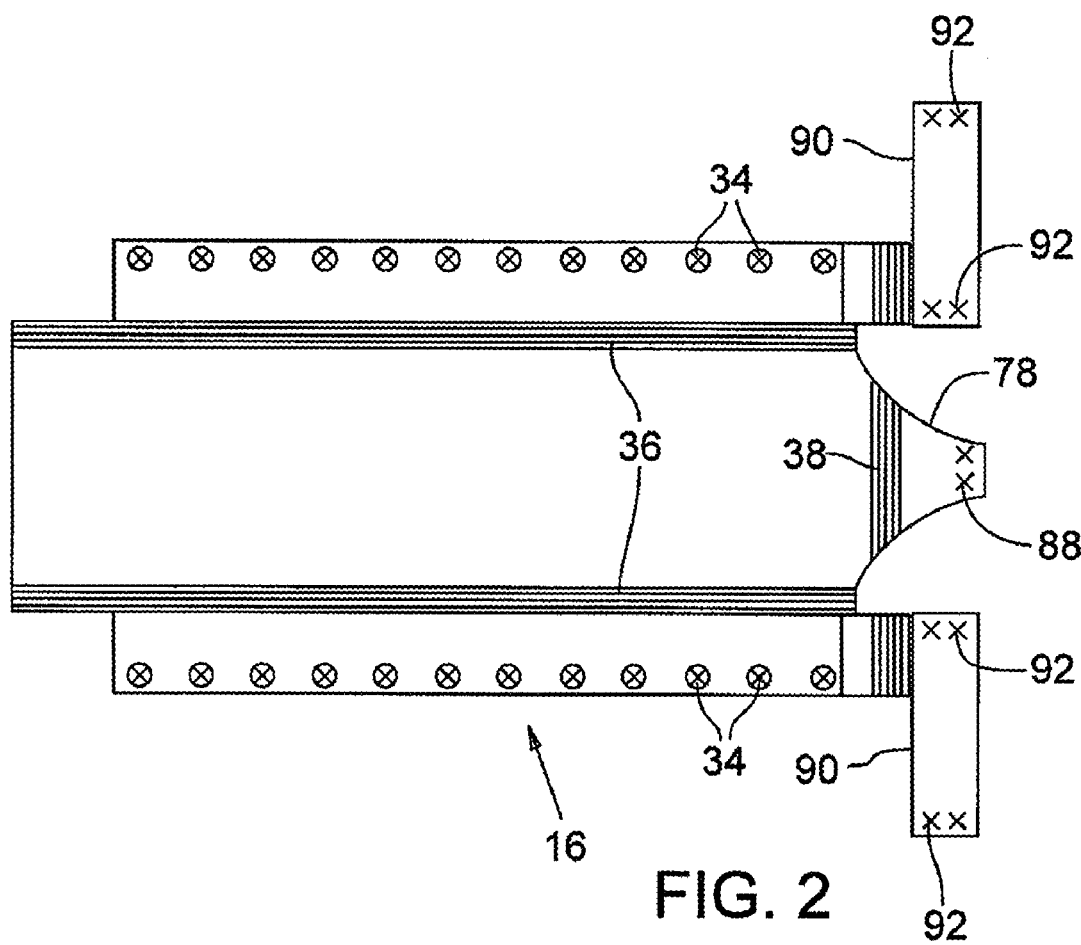
FIGS. 2 and 3 illustrate the components of the medical thermal cover of FIG. 1, including a bottom portion in FIG. 3 and a top portion in FIG. 2.

From FIG. 2 it will be observed that strips 90 may be provided as extensions of the bottom portion 16 of thermal cover 12. Fasteners 92 may be provided with e.g. mated snap fasteners, to permit wrapping of the strips 90 around a patient's thighs and then to fasten the fasteners at one end of the strip to the fasteners at the other end for securing the strips around the patient's thighs.

Strips 78 may be provided for both top and bottom thermal cover portions 14 and 16 and fasteners 88 as provided on the strips may be fastened together to secure the strips 78 at the groin area.

Figure 3:
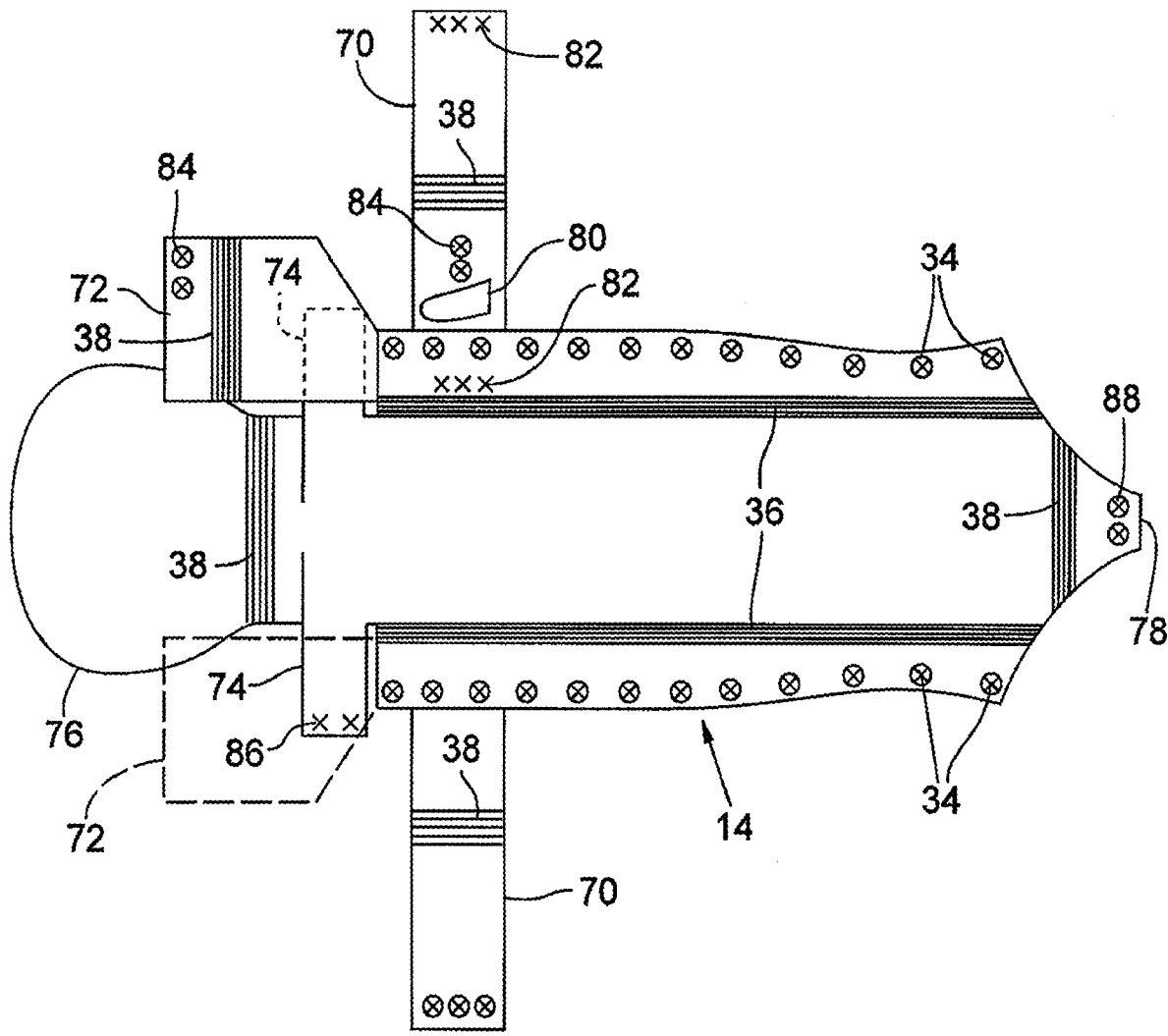

With reference to FIG. 3, strips 70, 72, and 74 may be extended from the top cover portion 14 and provide covering for the armpit areas, the shoulders and the neck area, respectively. As will be apparent, following fastening of the primary fasteners 34 to connect the top and bottom portions of the thermal cover, the neck covering 74 can be wrapped around the patient's neck and fastened together by fasteners 86. The armpit cover 70 is inserted down between the arm and chest areas and then wrapped up and around the outer side of the arm, with fasteners 82 of the strip secured to mated fasteners 82 on the main body portion 16. Then shoulder coverings 72 may be wrapped over the patient's shoulders with fasteners 84 on the shoulder strap fastened to mated fasteners 84 of the armpit wrap.

Returning to FIG. 1, it will be appreciated that each of the top and bottom thermal cover portions 14 and 16 contain thermal and electrical conductive areas (Primary and Secondary Zones for heating) which may include embedded electrical conductors, an example of which is disclosed in U.S. patent application Ser. No. 10/635,845. More recently, a material has been developed which itself is both heat and electrically conductive. Appropriate electrical connection is provided as illustrated by battery 40 with separate conductors 42, 44 connected to the top and bottom portions 14, 16, respectively. Control 46 controls energy directed to conductors 42, 44.

As explained, the Primary Zones for body areas 18, 20, 22, 24 (all located on the top thermal cover portion) are preferably provided with a greater fraction of the electrical power for heating than the one or more Secondary Zones (all located on the bottom thermal cover portion). Means to accomplish this have been previously described. Adjustment of control 46 allows the user to set the level of power through conductor 42 to the upper cover portion. Then, by design, one fourth of the power through conductor 42 is automatically delivered through conductor 44 to the bottom cover portion 16. Means of supplying different power levels to different zones has been previously described.

As an addition to the thermal cover (which may or may not cover the extremities), it may be desirable (particularly in cold climates) to place a space blanket or cover over the patient following installation of the thermal cover. Such space blanket is indicated by dash lines 48 in FIG. 1, and serves two purposes: a) it provides passive protection and warmth for the exposed limbs, by preventing direct environmental heat exchange and also by trapping heat leakage from the arm and leg ports of the thermal cover; and b) augments the inherent insulative properties of the thermal cover, especially when the space blanket is tucked around the sides and foot end of the subject. This extra cover can also be used to encase the head and/or the neck, or not, depending on environmental and medical conditions, such as the potential need of face access for medical management (e.g., needs to deal with airway maintenance, a respirator, oxygen administration, temperature measurement, and/or other issues) and attendant convenience.

In one embodiment, a thermal cover for supplying heat to a person experiencing or potentially subject to hypothermia, comprising: an upper portion (supine subject) covering primary body core areas, including a person's head, neck, chest, and abdomen and defining an upper portion circumferential side edge, and a lower portion covering a person's backside, including back and buttocks and defining a lower portion circumferential side edge; said upper and lower portions separable for permitting application thereof independently to a patient's front and back; fasteners for fastening the side edges together following independent application to the person and thereby said upper and lower portions being heat generating throughout most of the area of the covering in response to electrical connection; and a portable electric source controllably and independently connectable to said upper and lower portions and as connected providing selected greater heating of the upper portion than the lower portion.

In another embodiment, the upper and lower portions provide only partial covering of the person's extremities, and the chest area encompasses the shoulders and armpits of the person.

In another embodiment, the fasteners can be independently unfastened to expose a selective portion of the person's anatomy.

In another embodiment, expanders may be provided in the upper and/or lower portions to accommodate body size difference.

In another embodiment, a space cover overlies the body of the person in the thermal cover including the extremities not covered by the thermal cover.

In another embodiment, said expanders may be long and narrow non-heated strips, expandable in width and strategically placed to provide circumferential and elongation expansion to accommodate both girth and height differences and without interfering with heat conveyance to the primary core areas.

In another embodiment, heating therapy is actively controlled based on an integral system measure of core body temperature.

In another embodiment, the heating is directed selectively to the body core (internal organs; major blood vessels; brain).

In another embodiment, distinct sub-areas have been physiologically defined to permit optimizing the body surface uptake of applied heat per unit output of the system portable power source.

In another embodiment, a separate fuel-based pre-heater is included to allow warming the thermal cover in advance of subject insertion.

In another embodiment, the cover has been specially designed to be a single-use disposable.

In another embodiment, the therapeutic protocol is autonomous, once the subject has been inserted in the thermal cover and therapy has been initiated by an attendant.

Figure 4:
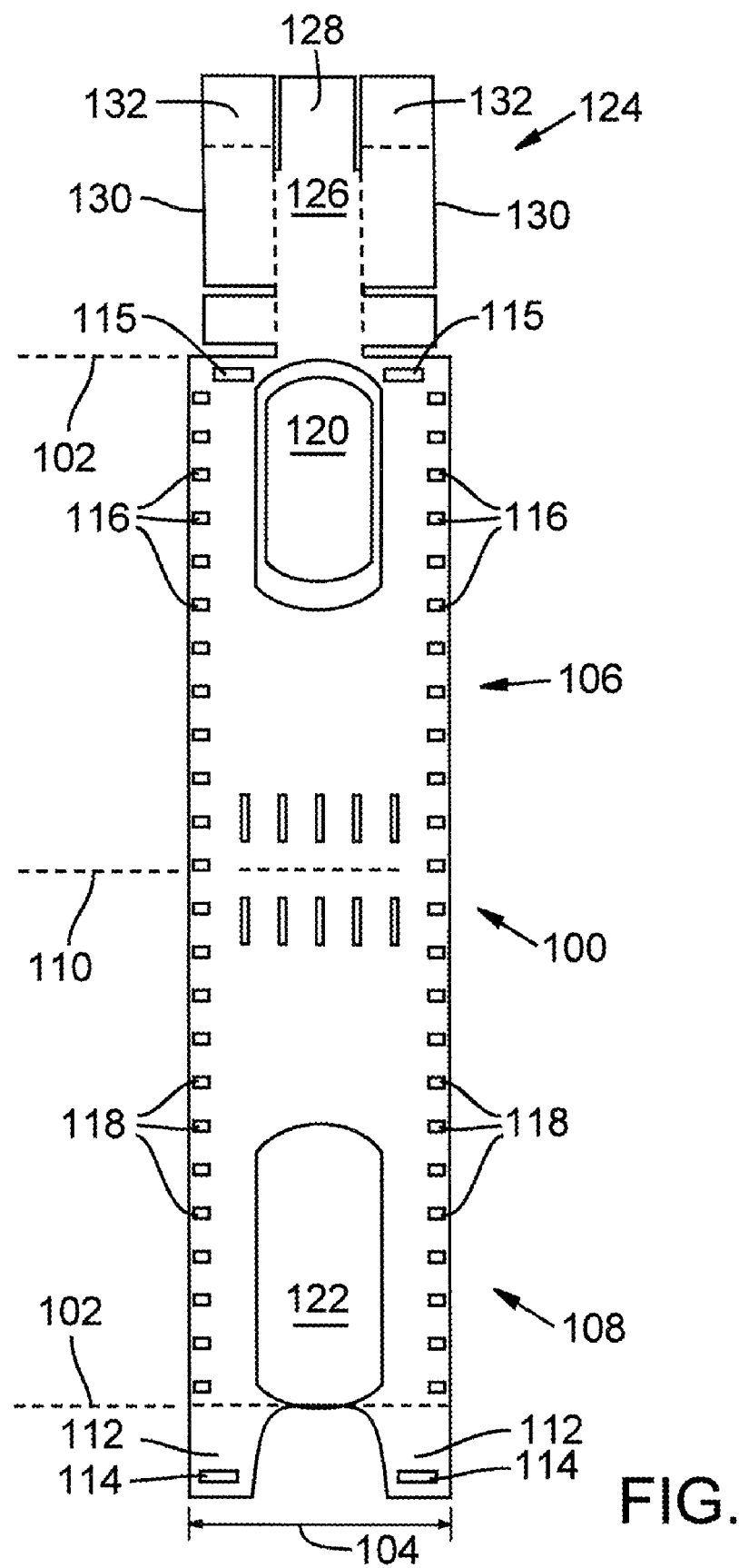
FIG. 4 illustrates a further embodiment as may be applied where less aggressive treatment may be desired.

Reference is now made to FIG. 4 which illustrates another embodiment of the present invention where a less aggressive approach may be. A single elongate blanket or covering 100 has a length 102 that may be twice the length of a tall person from shoulder to feet. Similarly, the covering 100 may have a width 104 that will extend beyond both sides of such a person's girth. The upper portion 106 as viewed in FIG. 4 may be designed to lie under a patient in a supine/lying down position and the lower portion 108 may be designed to fold from below the patient's feet e.g. at the point 110 and extend over the top of the patient where shoulder straps 112 can be folded over the patient's shoulder to engage the opposite side of the covering 100. In this relationship the quick release individual fasteners 114 can be engaged to secure the ends in the folded position. In this position, side fasteners 116 can be selectively engaged with fasteners 118.

As described, the patient's entire body below the head can be encased in a sleeping-bag-like casing or covering. However, the fastening system of fasteners 116/118 can be selectively not fastened or unfastened as desired to expose e.g. injured body portions for treatment or even to permit protrusion of arms and/or legs as desired.

Strategically positioned in both the upper and lower halves may be active heating zones 120, 122. These zones may be designed to substantially overlie and underlie the patient's chest and corresponding back area from his/her shoulder/neck down to the waist and, as desired, as far down as the user's crotch area or lower. In that this zone is fixed, the zone will be somewhat more extensive for smaller patients than for larger patients and such is taken into consideration in selecting the zone configuration.

It may also be desirable to provide a head covering 124 which may also include a zone or zones of active heating (no zone of active heating is shown in FIG. 4). The patient's head may lie in area 126, flap 128 folded over the top of the patient's head, and side flaps 130 folded against the sides of the patient's head with secondary fold flaps 132 folded onto flap 128, secured there e.g. by mated VELCRO™ strips. Further note the fasteners above and below center line 110 which can be fastened as desired to reduce the heating area as when accommodating smaller persons.

It will be appreciated that such a covering as illustrated in FIG. 4 may have some different advantages of the design of FIGS. 1-3. Many of the features may be retained such as whole body enclosure and selective access to areas of patient injury. It is considered far easier and quicker to apply, as the open "bag" can be simply laid on a surface, the patient laid e.g. on the upper portion of the bag (with the zone 120 centered on the patient's back) and the bottom portion folded up and over the patient. The heating zone 122 may be positioned on the patient's chest (and/or abdomen etc.) and the fasteners 114, 115 may be attached as well as selective ones of fasteners 116/118. A further alternative may be the provision of a hinge area (similar to hinge line 110 in FIG. 4) at side edge, and then provide fasteners along the bottom.

Where speed may be considered of utmost importance, the design of FIG. 4 may be a suitable option. As deemed desirable and/or appropriate, in various embodiments, various features of the design described in connection with FIGS. 1-3 may be incorporated into the design of FIG. 4.

It is to be understood that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein.

What is claimed is:

1. A portable heating system for treating a person suffering hypothermia at a site absent available electrical power comprising:

a covering having an under cover portion and an over cover portion, said under and over cover portions having multiple matable fasteners strategically and cooperatively arranged to aid in at least partial encasement of a person's torso with the person's head and the major portion of the person's limbs protruded from the covering;

said matable fasteners extended along one or more sides of said person's torso and individually releasable to permit selected exposure of the person's torso as may be desirable for treatment of an injury;

said under cover portion and said over cover portion having electrically induced controllable heating zones wherein primary heating zones are in the over cover portion and secondary heating zones are in the under cover portion, and wherein electrical input is converted into heat with the heating temperature substantially greater in the primary heating zones to enable optimizing the body surface uptake of applied heat per unit output of a portable battery;

said under and over cover portions adapted for battery generated power input for generating selective and proportionate heating to said electrically induced controllable heating zones; and further including the portable battery for providing said battery generated power input, said combination of battery and under and over cover portions designed for enabling manual transport to a remote location and thereat for maintaining and restoring normothermia during preparation, staging and transport from the remote location to a relevant medical facility.

2. A heating system as defined in claim 1 wherein the covering is provided with an opening for protrusion of said person's head and a head cover portion extended from said covering for covering the person's head.

3. A heating system as defined in claim 1 wherein said controllable primary and secondary heating zones have specified temperature differences, and a control for controlling the temperatures of said primary and secondary heating zones while maintaining said temperature differences.

4. A heating system as defined in claim 1 wherein said over and under cover portions fully surround the person's body and thereby defining matable edges, and said multiple fasteners extending fully along said matable edges for selective securement together of said over and under cover portions.

5. A heating system as defined in claim 4 including a control for controlling the heat generated in said heating zone.

\* \* \* \* \*